United States Patent [19]

Weissmuller et al.

[11] Patent Number: 4,904,656
[45] Date of Patent: Feb. 27, 1990

[54] 2-AMINOMETHYLTETRAHYDROFURANS, FUNGICIDAL COMPOSITIONS AND USE

[75] Inventors: Joachim Weissmuller, Monheim; Dieter Berg, Wuppertal; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 148,395

[22] Filed: Jan. 25, 1988

[30] Foreign Application Priority Data

Feb. 7, 1987 [DE] Fed. Rep. of Germany ....... 3703876
Sep. 17, 1987 [DE] Fed. Rep. of Germany ....... 3731198

[51] Int. Cl.$^4$ ................ A01N 43/08; A01N 43/84; C07D 307/14; C07D 413/06
[52] U.S. Cl. ................ 514/231.5; 514/326; 514/471; 544/152; 546/214; 549/472; 549/492
[58] Field of Search ............... 540/596, 597; 544/60, 544/124, 146, 152; 546/143, 205, 206, 212, 214, 268, 281, 283; 548/517, 527; 549/60, 378, 448, 472, 492; 514/212, 227.8, 231.5, 235.5, 318, 319, 326, 336, 343, 422, 444, 452, 467, 471

[56] References Cited

U.S. PATENT DOCUMENTS 4,414,216 11/1983 Kawakita et al. ................ 546/199
4,615,725 10/1986 Weissmuller et al. .

Primary Examiner—Robert W. Ramsuer
Attorney, Agent, or Firm—Sprung Horn Kramer & Woods

[57] ABSTRACT

Fungicidally active 2-aminomethyltetrahydrofurans of the formula

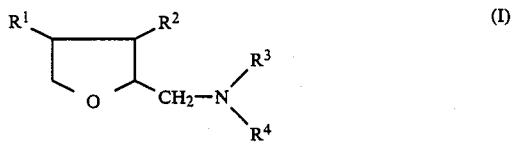

in which
$R^1$ represents in each case optionally substituted aryl, heteroaryl, cycloalkyl, tetrahydronaphthyl or decahydronaphthyl;
$R^2$ represents hydrogen or methyl; and
$R^3$ and $R^4$, independently of one another, in each case represent hydrogen, alkyl, alkenyl, alkinyl, alkoxyalkyl, dialkoxyalkyl, hydroxyalkyl, hydroxyalkoxyalkyl, dioxolanylalkyl, oxolanylalkyl, dioxanylalkyl, or in each case optionally substituted cycloalkylalkyl, cycloalkyl, aralkyl, aralkenyl or aryl, or
$R^3$ and $R^4$, together with the nitrogen atom to which they are bound, represent an optionally substituted saturated heterocyclic ring which may optionally contain further heteroatoms,
or acid-addition salts thereof.

10 Claims, No Drawings

2-AMINOMETHYLTETRAHYDROFURANS, FUNGICIDAL COMPOSITIONS AND USE

The invention relates to new 2-aminomethyltetrahydrofurans, several processes for their preparation, and their use as pesticides.

It has already been disclosed that certain aminomethyltetrahydrofurans, such as, for example, 2-(4-chlorophenyl)-5-(3,5-dimethylpiperidin-1-yl-methyl)-tetrahydrofuran, have fungicidal properties (cf. U.S. Pat. No. 4,615,725 issued Oct. 7, 1986.)

However, the activity of these previously known compounds is not completely satisfactory in all areas of application, in particular at low application rates and concentrations.

New 2-aminomethyltetrahydrofurans of the general formula (I)

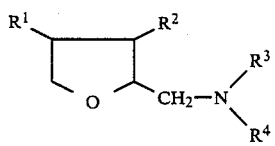

in which
$R^1$ represents in each case optionally substituted aryl, heteroaryl, cycloalkyl, tetrahydronaphthyl or decahydronaphthyl,
$R^2$ represents hydrogen or methyl, and
$R^3$ and $R^4$, independently of one another, in each case represent hydrogen, alkyl, alkenyl, alkinyl, alkoxyalkyl, dialkoxyalkyl, hydroxyalkyl, hydroxyalkoxyalkyl, dioxolanylalkyl, oxolanylalkyl, dioxanylalkyl or in each case optionally substituted cycloalkylalkyl, cycloalkyl, aralkyl, aralkenyl or aryl, or $R^3$ and $R^4$, together with the nitrogen atom to which they are bound, represent an optionally substituted saturated heterocyclic ring which may optionally contain further heteroatoms, and their plant-compatible acid-addition salts, have been found.

The compounds of the formula (I) can exist as geometrical and/or optical isomers or isomeric mixtures of varying composition. The pure isomers and the isomeric mixtures are covered by the invention.

It has furthermore been found that the new 2-aminomethyltetrahydrofurans of the general formula (I)

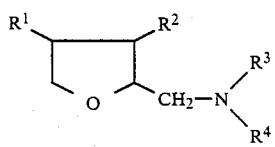

in which
$R^1$ represents in each case optionally substituted aryl, heteroaryl, cycloalkyl, decahydronaphthyl or tetrahydronaphthyl,
$R^2$ represents hydrogen or methyl, and
$R^3$ and $R^4$, independently of one another, in each case represent hydrogen, alkyl, alkenyl, alkinyl, alkoxyalkyl, dialkoxyalkyl, hydroxyalkyl, hydroxyalkoxyalkyl, dioxolanylalkyl, oxolanylalkyl, dioxanylalkyl or in each case optionally substituted cycloalkylalkyl, cycloalkyl, aralkyl, aralkenyl or aryl, or $R^3$ and $R^4$, together with the nitrogen atom to which they are bound, represent an optionally substituted saturated heterocyclic ring which may optionally contain further heteroatoms,
and their plant-compatible acid-addition salts, their geometrical and/or optical isomers and/or isomeric mixtures, are obtained when (a) substituted tetrahydrofurans of the formula (II)

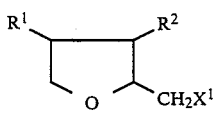

in which
$R^1$ and $R^2$ have the abovementioned meaning, and $X^1$ represents an electron-withdrawing leaving group, are reacted with amines of the formula (III)

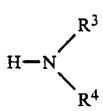

in which $R^3$ and $R^4$ have the abovementioned meaning, if appropriate in the presence of a diluent and if appropriate in the presence of an acid-binding agent; or when (b) the aminomethyltetrahydrofurans of the formula (Ia)

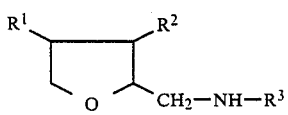

in which $R^1$, $R^2$ and $R^3$ have the abovementioned meaning, obtainable by process (a) and/or (c) are reacted with alkylating agents of the formula (IV)

in which
$R^{4-1}$ represents alkyl, alkenyl, alkinyl, alkoxyalkyl, dialkoxyalkyl, hydroxyalkyl, hydroxyalkoxyalkyl, dioxolanylalkyl, oxolanylalkyl, dioxanylalkyl or in each case optionally substituted cycloalkylalkyl, cycloalkyl, aralkyl or aralkenyl, and
$X^2$ represents an electron-withdrawing leaving group,
if appropriate in the presence of a diluent and if appropriate in the presence of an acid-binding agent; or when (c) the aminomethyltetrahydrofurans of the formula (Ib)

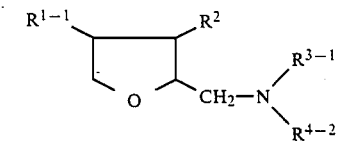

in which
$R^{1-1}$ represents optionally substituted aryl,
$R^2$ represents hydrogen or methyl,
$R^{3-1}$ and $R^{4-2}$, independently of one another, in each case represent hydrogen, alkyl, alkoxyalkyl, dialkoxyalkyl, hydroxyalkyl, hydroxyalkoxyalkyl, dioxolanylalkyl, oxolanylalkyl, dioxanylalkyl or in each case optionally substituted cycloalkyl, cycloalkylalkyl, aralkyl or aryl, or $R^{3-1}$ and $R^{4-2}$, together with the nitrogen atom to which they are bound, represent an optionally substituted saturated heterocyclic ring which may optionally contain further heteroatoms, obtainable by process (a) are hydrogenated in existing aryl substituents, if appropriate in the presence of a diluent and if appropriate in the presence of a catalyst and if appropriate under increased pressure; and if appropriate, an acid is subsequently added.

Finally, it has been found that the new aminomethyltetrahydrofurans of the general formula (I) have an action against pests, in particular against fungal pests.

Surprisingly, the 2-aminomethyltetrahydrofurans of the general formula (I) exhibit a better fungicidal activity than the aminomethyltetrahydrofurans which are known from the prior art, such as, for example, 2-(4-chlorophenyl)5-(3,5-dimethylpiperidin-1-yl-methyl)-tetrahydrofuran, which are similar compounds chemically and regarding their action.

Formula (I) provides a general definition of the aminomethyltetrahydrofurans according to the invention. Preferred compounds of the formula (I) are those in which $R^1$ represents phenyl which is optionally monosubstituted to polysubstituted by identical or different substituents, suitable substituents being: halogen, cyano, nitro, in each case straight-chain or branched alkyl, alkoxy, alkylthio, halogenoalkyl, halogenoalkoxy or halogenoalkylthio in each case having 1 to 6 carbon atoms and, if appropriate, 1 to 9 identical or different halogen atoms, amino, in each case straight-chain or branched alkylamino, dialkylamino or alkoximinoalkyl in each case having 1 to 4 carbon atoms in the individual alkyl parts; furthermore represents α-naphthyl or β-naphthyl which is in each case optionally monosubstituted to polysubstituted by identical or different substituents, suitable substituents in each case being: halogen, in each case straight-chain or branched alkyl or alkoxy in each case having 1 to 4 carbon atoms; furthermore represents cycloalkyl having 3 to 7 carbon atoms which is optionally monosubstituted to polysubstituted by identical or different substituents, suitable substituents being: in each case straight-chain or branched alkyl, alkoxy, halogenoalkyl or halogenoalkoxy in each case having 1 to 6 carbon atoms and, if appropriate, 1 to 9 identical or different halogen atoms; furthermore represents tetrahydronaphthyl or decahydronaphthyl which is in each case optionally monosubstituted to polysubstituted by identical or different substituents, suitable substituents for the hydrogenated rings being: straight-chain or branched alkyl and alkoxy in each case having 1 to 6 carbon atoms, and, in addition for the aromatic rings, halogen; and finally represents a 5- or 6-membered heteroaryl radical having 1 or 2 heteroatoms, in particular nitrogen, oxygen or sulphur, which is optionally monosubstituted to polysubstituted by identical or different substituents, suitable substituents in each case being: alkyl having 1 to 6 carbon atoms and/or halogen;

$R^2$ represents hydrogen or methyl, and $R^3$ and $R^4$, independently of one another, in each case represent hydrogen; in each case straight-chain or branched alkyl having 1 to 12 carbon atoms, alkenyl having 3 to 8 carbon atoms, alkinyl having 3 to 8 carbon atoms, hydroxyalkyl having 2 to 6 carbon atoms, alkoxyalkyl or dialkoxyalkyl in each case having 1 to 8 carbon atoms, or hydroxyalkoxyalkyl having 2 to 8 carbon atoms in the individual alkyl parts; in each case straight-chain or branched dioxolanylalkyl, oxolanylalkyl or dioxanylalkyl in each case having 1 to 4 carbon atoms in the alkyl part, or cycloalkyl or cycloalkylalkyl which has in each case 3 to 7 carbon atoms in the cycloalkyl part and, if appropriate, 1 to 4 carbon atoms in the straight-chain or branched alkyl part and is in each case optionally monosubstituted to polysubstituted in the cycloalkyl part by identical or different substituents, suitable substituents in each case being: halogen, in each case straight-chain or branched alkyl, alkoxy, halogenoalkyl or halogenoalkoxy in each case having 1 to 4 carbon atoms and, if appropriate, 1 to 9 identical or different halogen atoms; in addition represents arylalkyl, arylalkenyl or aryl which has in each case 6 to 10 carbon atoms in the aryl part and, if appropriate, up to 6 carbon atoms in the straight-chain or branched alkyl or alkenyl part and which is in each case optionally monosubstituted to polysubstituted by identical or different substituents, suitable aryl substituents in each case being: halogen, cyano, nitro, in each case straight-chain or branched alkyl, alkoxy, alkylthio, halogenoalkyl, halogenoalkoxy, halogenoalkylthio or alkoximinoalkyl in each case having 1 to 4 carbon atoms in the individual alkyl parts and, if appropriate, 1 to 9 identical or different halogen atoms; or $R^3$ and $R^4$, together with the nitrogen atom to which they are bound, represent a 5- to 7-membered heterocyclic ring which may optionally contain a further heteroatom, in particular nitrogen, oxygen or sulphur, and is optionally monosubstituted or polysubstituted by identical or different substituents, suitable substituents being: in each case straight-chain or branched alkyl or hydroxyalkyl in each case having 1 to 4 carbon atoms.

Particularly preferred compounds of the formula (I) are those in which $R^1$ represents phenyl which is in each case optionally monosubstituted, disubstituted or trisubstituted by identical or different substituents, suitable substituents being: fluorine, chlorine, bromine, iodine, cyano, nitro, methyl, ethyl, n-or i-propyl, n-, i-, s- or t-butyl, n- or i-pentyl, n- or i-hexyl, methoxy, ethoxy, t-butoxy, trifluoromethyl, trifluoromethylthio, trifluoromethoxy, methoximinomethyl, dimethylamino and diethylamino; furthermore represents α-naphthyl or β-naphthyl which is in each case optionally monosubstituted, disubstituted or trisubstituted by identical or different substituents, suitable substituents in each case being: fluorine, chlorine, bromine, iodine, methyl, ethyl, n- or i-propyl, n-, i-, s- or t-butyl, methoxy and ethoxy; furthermore represents cyclopentyl or cyclohexyl which is in each case optionally monosubstituted, disubstituted or trisubstituted by identical or different substituents, suitable substituents in each case being: methyl, ethyl, n- or i-propyl, n-, i-, s- or t-butyl, n- or i-pentyl, methoxy, ethoxy, t-butoxy, trifluoromethyl and difluoromethoxy;

furthermore represents tetrahydronaphthyl which is optionally monosubstituted, disubstituted or trisubstituted by identical or different substituents, suitable substituents being: fluorine, chlorine, bromine, methyl, ethyl, n- or i-propyl, n-, i-, s-or t-butyl, methoxy and ethoxy;

furthermore represents decahydronaphthyl which is optionally monosubstituted, disubstituted or trisubstituted by identical or different substituents, suitable substituents being: methyl, ethyl, n- or i-propyl, n-, i-, s- or t-butyl, methoxy and ethoxy;

or represents 2-, 3- or 4-pyridyl and 2- or 3-thienyl which is in each case optionally monosubstituted, disubstituted or trisubstituted by identical or different substituents, suitable substituents in each case being: fluorine, chlorine, bromine, methyl, ethyl, n- or i-propyl, n-, i-, s-and t-butyl;

$R^2$ represents hydrogen or methyl, and $R^3$ and $R^4$, independently of one another, in each case represent hydrogen, methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, dioxolanylmethyl, dioxolanylethyl, oxolanylmethyl, oxolanylethyl, dioxanylmethyl, dioxanylethyl, or represents cyclopropyl, cyclopropylmethyl, cyclopropylethyl, cyclopropylpropyl, cyclopentyl, cyclopentylmethyl, cyclohexyl or cyclohexylmethyl which is in each case optionally monosubstituted to pentasubstituted by identical or different substituents, suitable substituents in each case being fluorine, chlorine, bromine, methyl, ethyl, n- or i-propyl, n-, i-, s- and/or t-butyl, or represents phenyl, benzyl or phenylethyl which is in each case optionally monosubstituted, disubstituted or trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, methylthio, trifluoromethoxy, trifluoromethylthio, methoxycarbonyl, or methoximinomethyl; or $R^3$ and $R^4$, together with the nitrogen atom to which they are bound, represent a heterocyclic ring of the formula

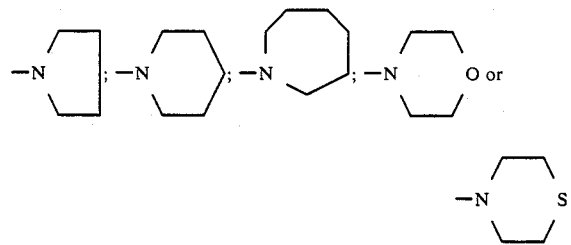

which is optionally monosubstituted, disubstituted or trisubstituted by identical or different substituents, suitable substituents being: methyl, ethyl or hydroxymethyl.

In addition to the compounds mentioned in the preparation examples, the following 2-aminomethyltetrahydrofurans of the general formula (I) may be mentioned individually;

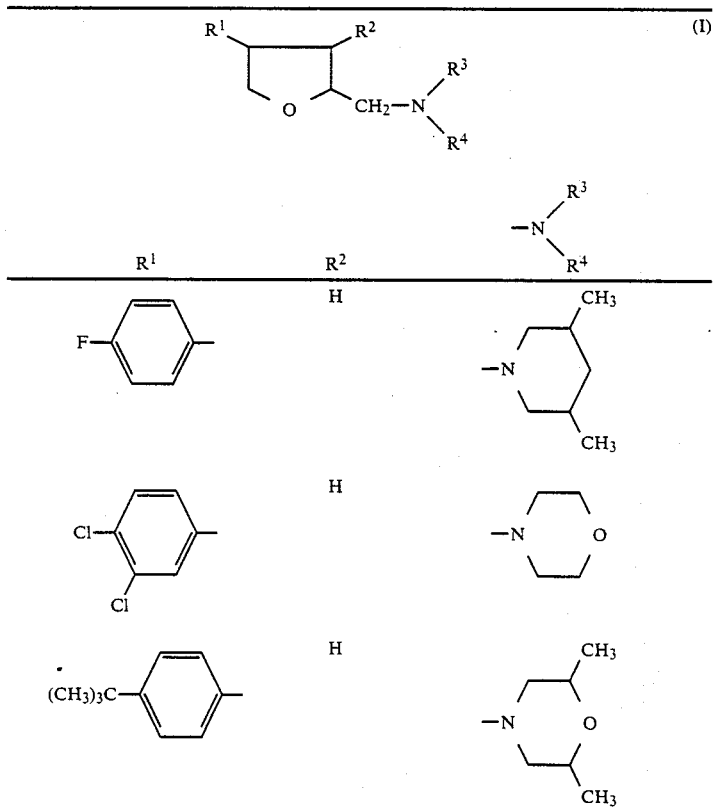

-continued $$\text{(I)}$$

Structure: tetrahydrofuran ring with R¹ at 4-position, R² at 3-position, and CH₂-N(R³)(R⁴) at 2-position.

| R¹ | R² | −N(R³)(R⁴) |
|---|---|---|
| (CH₃)₃C−C₆H₄− | H | −NH−(CH₂)₃−OCH₃ |
| (CH₃)₃C−C₆H₄− | H | −NH−(CH₂)₃−OC₂H₅ |
| (CH₃)₃C−C₆H₄− | H | −N(CH₃)−CH₂−CH(CH₃)₂ |
| (CH₃)₃C−C₆H₄− | H | −N(CH₃)−CH₂−CH(C₂H₅)₂ |
| (CH₃)₃C−C₆H₄− | H | −NH−C₆H₁₁ (cyclohexyl) |
| (CH₃)₃C−C₆H₄− | H | −N(C₃H₇)−(CH₂)₃−OCH₃ |
| (CH₃)₃C−C₆H₄− | H | −NH−(CH₂)₂−O−(CH₂)₂−OH |
| (CH₃)₃C−C₆H₄− | H | −NH−CH₂−CH(OCH₃)₂ |
| (CH₃)₃C−C₆H₄− | H | −NH−CH₂−CH(OC₂H₅)₂ |
| (CH₃)₃C−C₆H₄− | H | −N(piperidinyl) |
| (CH₃)₃C−C₆H₄− | H | −N(3-methylpiperidinyl) |

-continued
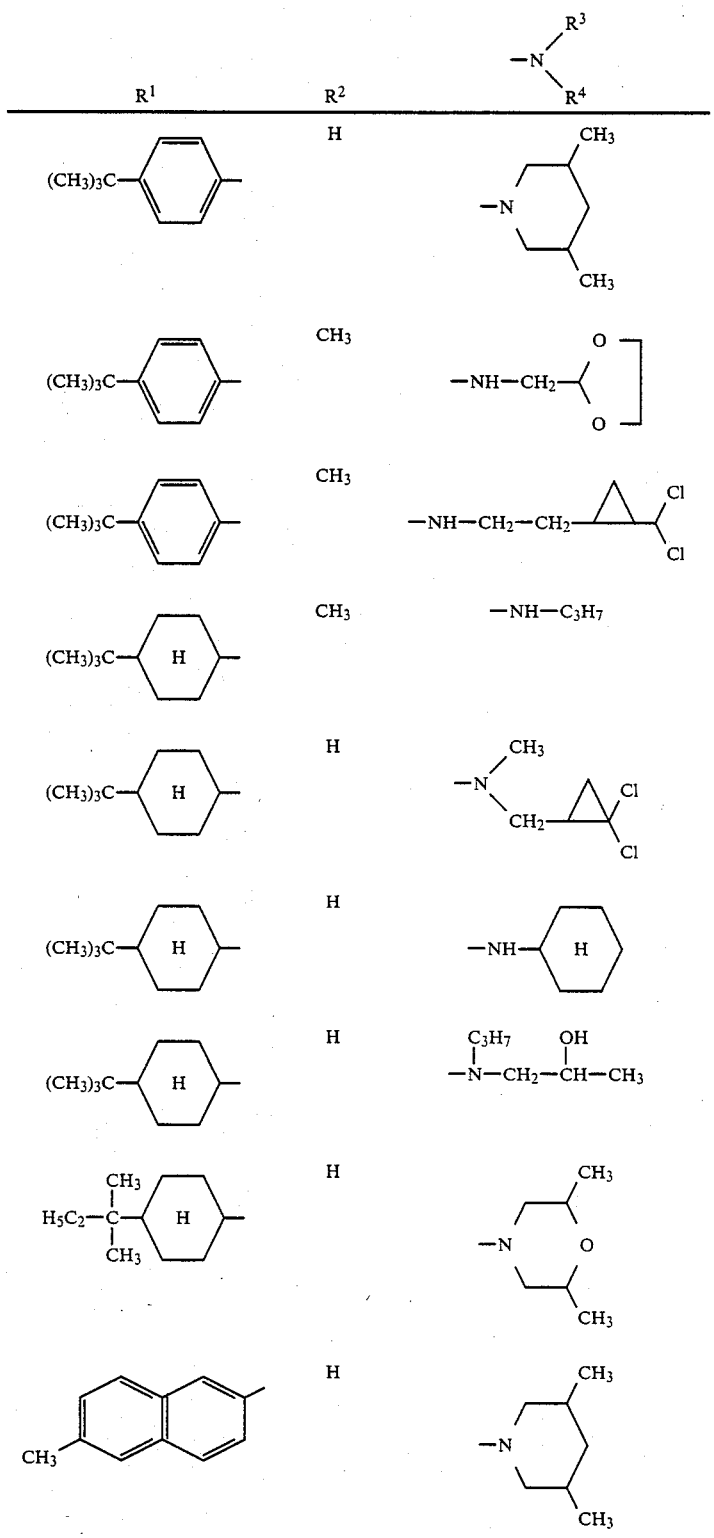

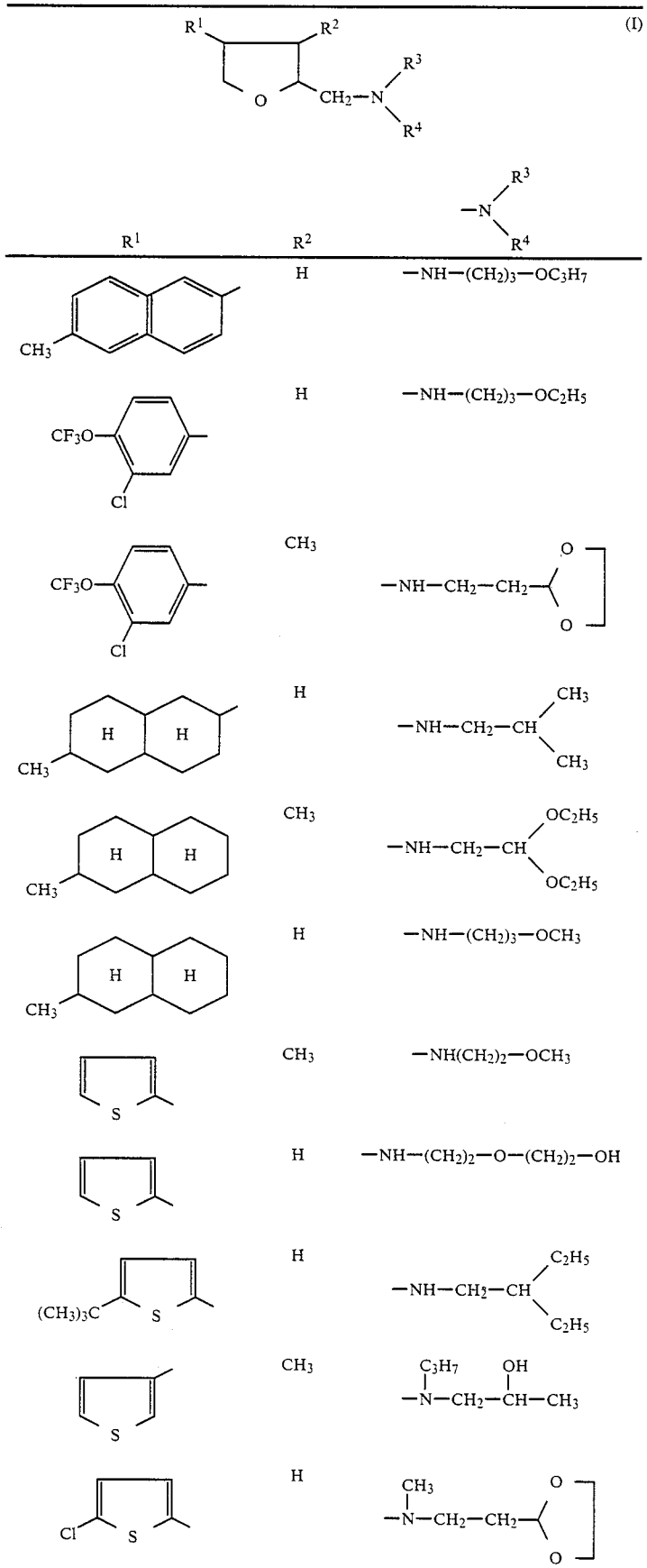

-continued $$\begin{array}{c} R^1 \quad R^2 \\ \diagup \quad \diagup \\ \text{O} \quad \text{CH}_2-\text{N} \diagdown \begin{array}{c} R^3 \\ R^4 \end{array} \end{array} \quad (I)$$

| R¹ | R² | $-N\begin{array}{c}R^3\\R^4\end{array}$ |
|---|---|---|
| 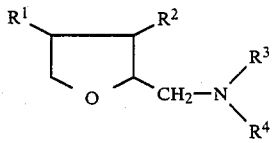 (5-bromo-2-thienyl with methyl) | H | —NH—C₄H₉—n |
| 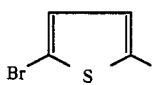 (5-tert-butyl-2-thienyl) | H | —NH—CH₂—CH(OC₂H₅)₂ |
| 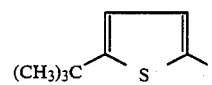 (5-tert-butyl-2-thienyl) | H | $-N(CH_3)-CH_2-CH\begin{array}{c}O\\ \diagdown\\O\end{array}$ (1,3-dioxolane) |
| 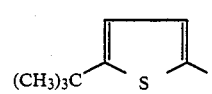 (4-tert-butylphenyl) | H | $-N(CH_3)-CH_2-$ 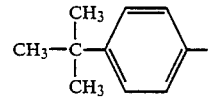 (2,2-dichlorocyclopropyl) |
| 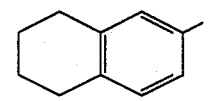 (5,6,7,8-tetrahydronaphthyl) | H | 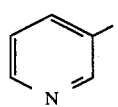 (piperidino) |
|  (3-pyridyl) | H | —NH—CH₂—CH(CH₃)₂ |
|  (3-pyridyl) | CH₃ | 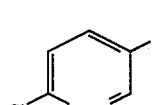 (2,6-dimethylmorpholino) |
| 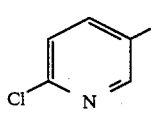 (3-pyridyl) | H |  (3,5-dimethylpiperidino) |
| 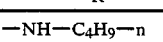 (6-chloro-3-pyridyl) | H | —N(C₃H₇)—(CH₂)₂—O—(CH₂)₂—OH |
| 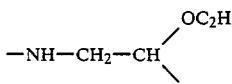 (6-chloro-3-pyridyl) | H | —NH—CH₂—CH(OCH₃)₂ |

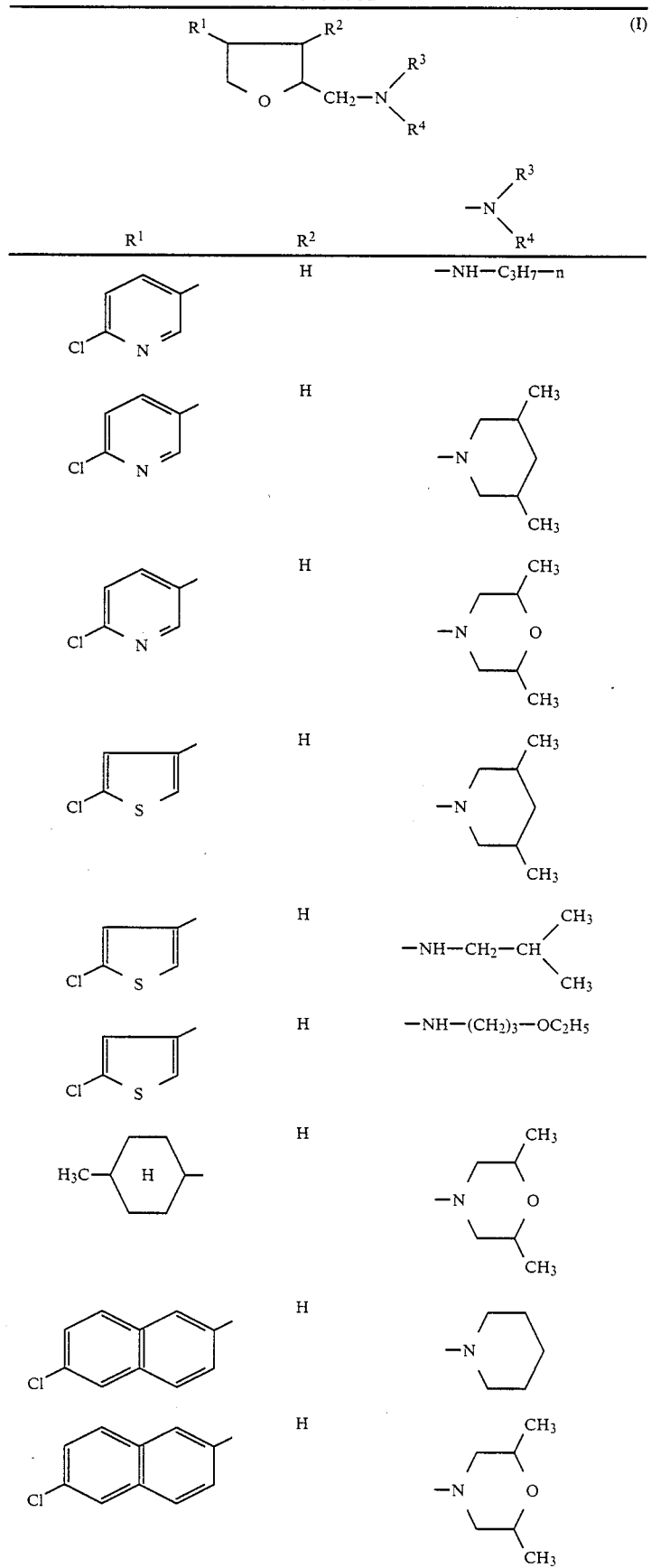

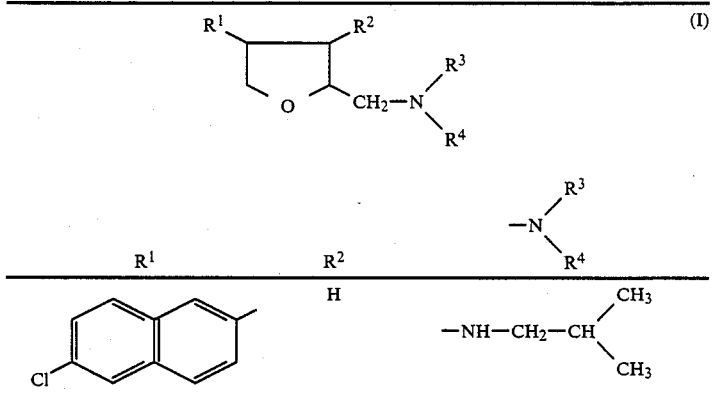

If, for example, 2-bromomethyl-4-cyclohexyltetrahydrofuran and piperidine are used as starting materials, the course of the reaction of process (a) according to the invention may be represented by the following equation:

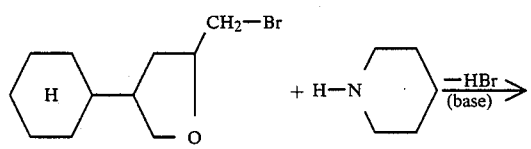

If, for example, 2-cyclohexylaminomethyl-4-[4-tert.butylcyclohexyl]-tetrahydrofuran and allyl bromide are used as starting materials, the course of the reaction of process (b) according to the invention may be represented by the following equation:

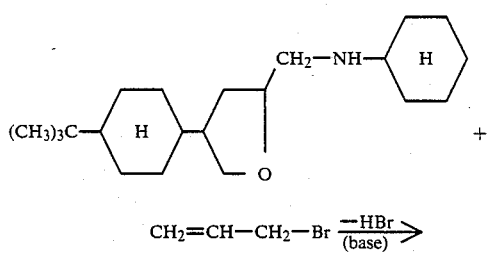

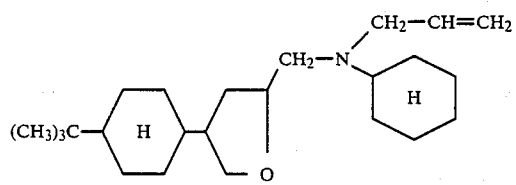

If, for example, 2-(morpholin-4-yl-methyl)-4-(4-tert.-butyl-phenyl)-tetrahydrofuran is used as starting material and hydrogen is used as hydrogenating agent, the course of the reaction of process (c) according to the invention may be represented by the following equation:

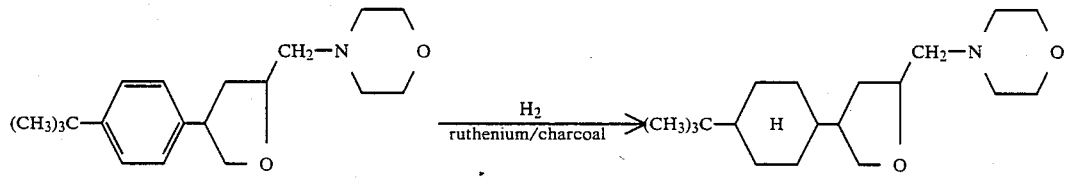

Formula (II) provides a general definition of the substituted tetrahydrofurans which are required as starting materials for carrying out process (a) according to the invention. In this formula (II), $R^1$ and $R^2$ preferably represent those radicals which have already been mentioned in connection with the description of the substances of the formula (I) according to the invention as being preferred for these substituents.

$X^1$ preferably represents halogen, in particular chlorine or bromine, or in each case optionally substituted alkylsulphonyloxy or arylsulphonyloxy, such as, for example, methanesulphonyloxy or p-toluenesulphonyloxy, The substituted tetrahydrofurans of the formula (II) are known (cf., for example, EP-OS (European Published Specification) 68,331 and J. Org. Chem. 49(9), 1557–59) or can be obtained in a generally known fashion, for example in a process in which generally known esters of the formula (V)

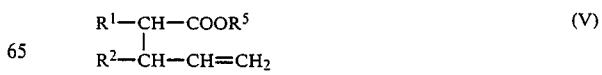

in which

R$^1$ and R$^2$ have the abovementioned meaning, and

R$^5$ represents alkyl or optionally substituted aryl, are reacted with a reducing agent, such as, for example, lithium aluminum hydride, if appropriate in the presence of a diluent, such as, for example, diethyl ether, at temperatures between −20° C. and +80° C.; the carbinols of the formula (VI)

in which R$^1$ and R$^2$ have the abovementioned meaning, thus obtained are subsequently reacted either with a halogenating agent, such as, for example, elemental bromine, in the presence of quinoline, or with N-bromosuccinimide, if appropriate in the presence of a diluent, such as, for example, chloroform, at temperatures between −20° C. and +80° C., or converted by generally conventional processes, such as, for example, by reaction with hydrogen peroxide/formic acid, into a trihydroxy compound of the formula (VII)

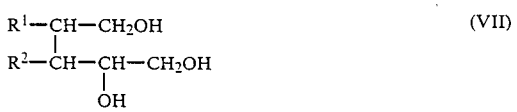

in which R$^1$ and R$^2$ have the abovementioned meaning, and this is reacted, in situ or after intermediate isolation in a generally known fashion, with water-eliminating reagents, such as, for example, sulphuric acid, if appropriate in the presence of a diluent, such as, for example, toluene, at temperatures between −10° C. and 120° C.; and the tetrahydrofurans of the formula (VIII)

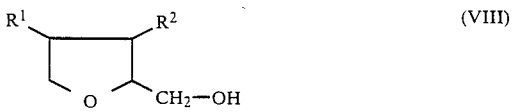

in which R$^1$ and R$^2$ have the abovementioned meaning, thus obtained are subsequently reacted with conventional halogenating agents, such as, for example, phosphorus tribromide or with generally known sulphonyl halides of the formula (IX)

in which

R$^6$ represents in each case optionally substituted alkyl or aryl, in particular methyl, trifluoromethyl or p-tolyl, and Hal represents halogen, in particular chlorine, bromine or iodine, if appropriate in the presence of a diluent, such as, for example, dichloromethane, and if appropriate in the presence of an acid-binding agent, such as, for example, pyridine, at temperatures between 0° C. and 120° C.

Formula (III) provides a general definition of the amines furthermore required as starting materials for carrying out process (a) according to the invention. In this formula (III), R$^3$ and R$^4$ preferably represent those radicals which have already been mentioned in connection with the description of the substances of the formula (I) according to the invention as being preferred for these substituents.

The amines of the formula (III) are generally known compounds of organic chemistry.

Formula (Ia) provides a general definition of the aminomethyltetrahydrofurans required as starting materials for carrying out process (b) according to the invention. In this formula (Ia), R$^1$, R$^2$ and R$^3$ preferably represent those radicals which have already been mentioned in connection with the description of the substances of the formula (I) according to the invention as being preferred for these substituents.

The aminomethyltetrahydrofurans of the formula (Ia) are compounds according to the invention and can be obtained with the aid of process (a) according to the invention.

Formula (IV) provides a general definition of the alkylating agents furthermore required as starting materials for carrying out process (b) according to the invention. In this formula (IV), R$^{4\text{-}1}$ preferably represents in each case straight-chain or branched alkyl having 1 to 12 carbon atoms, alkenyl having 3 to 8 carbon atoms, alkinyl having 3 to 8 carbon atoms, hydroxyalkyl having 2 to 6 carbon atoms, alkoxyalkyl, dialkoxyalkyl or hydroxyalkoxyalkyl in each case having 1 to 6 carbon atoms in the individual alkyl parts, dioxolanylalkyl, oxolanylalkyl or dioxanylalkyl in each case having 1 to 4 carbon atoms in the straight-chain or branched alkyl part, cycloalkyl or cycloalkylalkyl which in each case has 3 to 7 carbon atoms in the cycloalkyl part and, if appropriate, 1 to 4 carbon atoms in the straight-chain or branched alkyl part and is in each case optionally monosubstituted to polysubstituted in the cycloalkyl part by identical or different substituents, suitable substituents in each case being: halogen, in each case straight-chain or branched alkyl, alkoxy, halogenoalkyl or halogenoalkoxy in each case having 1 to 4 carbon atoms and, if appropriate, 1 to 9 identical or different halogen atoms; in addition represents arylalkyl or arylalkenyl which has in each case 6 to 10 carbon atoms in the aryl part and up to 6 carbon atoms in the straight-chain or branched alkyl or alkenyl part and which is in each case optionally monosubstituted to polysubstituted in the aryl part by identical or different substituents, suitable aryl substituents in each case being: halogen, cyano, nitro, in each case straight-chain or branched alkyl, alkoxy, alkylthio, halogenoalkyl, halogenoalkoxy, halogenoalkylthio, alkoxycarbonyl or alkoximinoalkyl in each case having 1 to 4 carbon atoms in the individual alkyl parts and, if appropriate, 1 to 9 identical or different halogen atoms;

R$^{4\text{-}1}$ particularly preferably represents methyl, ethyl, n- or i-propyl, n-, i-, s- or t-butyl, n-or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, dioxolanylmethyl, dioxolanylethyl, oxolanylmethyl, oxolanylethyl, dioxanylmethyl, dioxanylethyl, or represents cyclopropyl, cyclopropylmethyl, cyclopropylethyl, cyclopropypropyl, cyclopentyl, cyclopentylmethyl, cyclohexyl or cyclohexylmethyl which is in each case optionally monosubstituted to pentasubstituted by identical or different substituents, suitable substituents in each case being fluorine, chlorine, bromine, methyl, ethyl, n- or i-propyl, n-, i-, s- and/or t-butyl, or represents benzyl or phenylethyl which is in each case optionally monosubstituted, disubstituted or trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, methylthio, trifluoromethoxy, trifluoromethylthio, methoxycarbonyl, ethoxycarbonyl or methoximinomethyl, $R^{4-1}$ very particularly preferably represents methyl, ethyl, n- or i-propyl, n-, i-, s- or t-butyl, n- or i-pentyl, n- or i-hexyl, allyl, n-or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, dioxolanylmethyl, dioxolanylethyl, dioxanylmethyl, cyclopropylmethyl, dichlorocyclopropylmethyl, dimethylcyclopropylmethyl, dichlorodimethylcyclopropylmethyl, cyclopentyl, cyclohexyl or cyclohexylmethyl, and $X^2$ preferably represents halogen, in particular chlorine, bromine or iodine, or in each case optionally substituted alkylsulphonyloxy, alkoxysulphonyloxy or arylsulphonyloxy, such as, for example, methanesulphonyloxy, methoxysulphonyloxy or p-toluenesulphonyloxy.

The alkylating agents of the formula (IV) are generally known compounds of organic chemistry or can be obtained analogously to generally known processes.

Formula (Ib) provides a general definition of the aminomethyltetrahydrofurans required as starting materials for carrying out process (c) according to the invention.

In this formula (Ib), $R^{1-1}$ preferably represents phenyl which is optionally monosubstituted to polysubstituted by identical or different substituents, suitable substituents being: halogen, cyano, nitro, in each case straight-chain or branched alkyl, alkoxy, alkylthio, halogenoalkyl, halogenoalkoxy or halogenoalkylthio in each case having 1 to 6 carbon atoms and, if appropriate, 1 to 9 identical or different halogen atoms, amino, in each case straight-chain or branched alkylamino, dialkylamino or alkoximinoalkyl in each case having 1 to 4 carbon atoms in the individual alkyl parts; furthermore represents α-naphthyl or β-naphthyl which is in each case optionally monosubstituted to polysubstituted by identical or different substituents, suitable substituents in each case being: halogen, in each case straight-chain or branched alkyl or alkoxy in each case having 1 to 4 carbon atoms;

$R^2$ preferably represents hydrogen or methyl;

$R^{3-1}$ and $R^{4-2}$, independently of one another, preferably represent hydrogen; in each case straight-chain or branched alkyl having 1 to 12 carbon atoms, hydroxyalkyl having 2 to 6 carbon atoms, alkoxyalkyl or dialkoxyalkyl in each case having 1 to 8 carbon atoms or hydroxyalkoxyalkyl having 2 to 8 carbon atoms in the individual alkyl parts; straight-chain or branched dioxolanylalkyl, oxolanylalkyl or dioxanylalkyl in each case having 1 to 4 carbon atoms in the alkyl part, or cycloalkyl or cycloalkylalkyl which has in each case 3 to 7 carbon atoms in the cycloalkyl part and, if appropriate, 1 to 4 carbon atoms in the straight-chain or branched alkyl part and which is in each case optionally monosubstituted or polysubstituted in the cycloalkyl part by identical or different substituents, suitable substituents in each case being: halogen, in each case straight-chain or branched alkyl, alkoxy, halogenoalkyl or halogenoalkoxy in each case having 1 to 4 carbon atoms and, if appropriate, 1 to 9 identical or different halogen atoms; in addition represents arylalkyl or aryl which has in each case 6 to 10 carbon atoms in the aryl part and, if appropriate, up to 6 carbon atoms in the straight-chain or branched alkyl part and which is in each case optionally monosubstituted to polysubstituted in the aryl part by identical or different substituents, suitable aryl substituents in each case being the abovementioned cycloalkyl substituents; or $R^{3-1}$ and $R^{4-2}$, together with the nitrogen atom to which they are bound, preferably represent a saturated 5- to 7-membered heterocyclic ring which may optionally contain a further heteroatom, in particular nitrogen, oxygen or sulphur, and which is optionally monosubstituted to polysubstituted by identical or different substituents, suitable substituents being: in each case straight-chain or branched alkyl or hydroxyalkyl in each case having 1 to 4 carbon atoms.

The aminomethyltetrahydrofurans of the formula (Ib) are substances according to the invention and can be obtained according to process (a).

Suitable diluents for carrying out processes (a) and (b) according to the invention are inert organic solvents or aqueous systems. These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethylether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Processes (a) and (b) according to the invention may, if appropriate, alternatively be carried out in a two-phase system, such as, for example, water/toluene or water/dichloromethane, if appropriate in the presence of a phase-transfer catalyst. Examples of such catalysts which may be mentioned are: tetrabutylammonium iodide, tetrabutylammonium bromide, tributyl-methyl-phosphonium bromide, trimethyl-$C_{13}/C_{15}$-alkylammonium chloride, dibenzyldimethyl-ammonium methylsulphate, dimethyl-$C_{12}/C_{14}$-alkyl-benzylammonium chloride, tetrabutylammonium hydroxide, 15-crown-5, 18-crown-6, triethylbenzylammonium chloride and trimethylbenzylammonium chloride. It is also possible to carry out processes (a) and (b) according to the invention without adding a solvent.

Suitable acid-binding agents for carrying out processes (a) and (b) according to the invention are all inorganic and organic bases which can conventionally be used. Alkali metal hydroxides, carbonates or hydrogen carbonates, such as, for example, sodium hydroxide, sodium carbonate or sodium hydrogen carbonate, or alternatively tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU) are preferably used.

It is also possible to employ, in a suitable excess, the amines of the formulae (III) or (Ia) used as reaction participants simultaneously as acid-binding agents.

The reaction temperatures may be varied within a relatively wide range when carrying out processes (a) and (b) according to the invention. In general, the processes are carried out at temperatures between −20° C. and +180° C., preferably at temperatures between 20° C. and +150° C.

In order to carry out process (a) according to the invention, 1.0 to 3.0 mols, preferably 1.0 to 1.5 mols, of amine of the formula (III) and, if appropriate, 1.0 to 3.0 mols, preferably 1.0 to 1.5 mols, of acid-binding agent, and, if appropriate, 0.1 to 1.0 mol of phase-transfer catalyst are generally employed per mol of substituted tetrahydrofuran of the formula (II).

In order to carry out process (b) according to the invention, 1.0 to 5.0 mols, preferably 1.0 to 2.0 mols, of alkylating agent of the formula (IV) and 1.0 to 5.0 mols, preferably 1.0 to 2.0 mols, of acid-binding agent, and, if appropriate, 0.1 to 1.0 mol of phase-transfer catalyst are generally employed per mol of aminomethyltetrahydrofuran of the formula (Ia). The reaction is carried out and the reaction products of the formula (I) are worked up and isolated in both cases by conventional methods.

Possible diluents when carrying out process (c) according to the invention are all solvents which are inert under hydrogenation conditions. Hydrocarbons, such as petroleum ether, pentane, hexane, heptane and cyclohexane, alcohols, such as methanol, ethanol, n-propanol and i-propanol, or ethers, such as diethyl ether, dioxane, tetrahydrofuran or ethylene glycol dimethyl or diethyl ether, can preferably be used. However, the process can also be carried out without diluent.

Suitable hydrogenating agents when carrying out process (c) according to the invention are those compounds which are able to hydrogenate aromatics. Molecular hydrogen is preferably used.

Hydrogenation catalysts which can be employed in process (c) according to the invention are all catalysts which can conventionally be used for such reactions. Raney nickel or noble metal catalysts, such as palladium, ruthenium, palladium oxide, platinum or platinum oxide, if appropriate on a suitable support, such as, for example, charcoal, are preferably used.

The reaction temperatures may be varied within a relatively wide range when carrying out process (c) according to the invention. In general, the process is carried out at temperatures between 50° C. and 250° C., preferably at temperatures between 80° C. and 200° C.

Process (c) according to the invention can be carried out at atmospheric pressure, or alternatively at increased pressure. The process is preferably carried out under increased pressure in the presence of hydrogen. In general, pressure ratios between 5 and 300 atm, preferably between 10 and 200 atm, are used.

When carrying out process (c) according to the invention, 3.0 to 30 moles of hydrogenating agent and 0.001 to 0.1 mole, preferably 0.01 to 0.1 mole, of catalyst are generally employed per mole of aminomethyltetrahydrofuran of the formula (Ib).

When carrying out process (c) according to the invention, a procedure is generally followed in which the compounds of the formula (Ib) are reacted with hydrogen in an autoclave at the temperature desired in each case in the presence of a diluent. Work-up is effected by conventional methods.

The following acids are preferably suitable for the preparation of acid-addition salts of the compounds of the formula (I): hydrohalic acids, such as, for example, hydrochloric acid and hydrobromic acid, in particular hydrochloric acid, furthermore phosphoric acid, nitric acid, sulphuric acid, mono-, bi- and tri-functional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid and 1,5-naphthalenedisulphonic acid, and also saccharin.

The acid-addition salts of the compounds of the formula (I) can be obtained in a simple fashion by conventional salt-formation methods, such as, for example, by dissolving a compound of the formula (I) in a suitable inert solvent and adding the acid, such as, for example, hydrochloric acid, and can be isolated in a known fashion, for example by filtering off, and purified, if appropriate, by washing with an inert organic solvent.

The active compounds according to the invention have a strong action against pests and can be employed in practice for combating undesired harmful organisms. The active compounds are suitable for use, inter alia, as plant-protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, Tilletia caries; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The new active compounds can be employed particularly successfully for combating cereal diseases, such as, for example, *Erysiphe graminis, Septoria nodorum, Cochliobolus sativus* and *Pyrenophora teres*. In addition, the compounds of the formula (I) exhibit a good action against rice diseases, such as *Pyricularia oryzae*, and also a broad fungicidal in vitro activity.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; with liquefied gaseous, extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

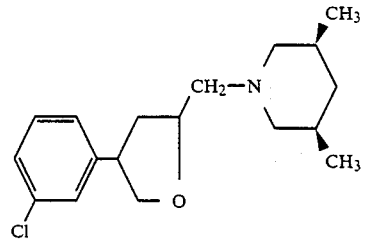

A mixture of 20 g (0.073 mol) of 2-bromomethyl-4-(3-chlorophenyl)-tetrahydrofuran and 17 g (0.147 mol) of cis-3,5-dimethylpiperidine is stirred for 16 hours at a bath temperature of 120° C., cooled and taken up in a mixture of diethyl ether and water; the organic phase is separated off, dried over sodium sulphate and concentrated in vacuo, and the residue is chromatographed over silica gel.

8.3 g (37% of theory) of 2-(3,5-cis-dimethylpiperidin-1-yl-methyl)-4-(3-chlorophenyl)-tetrahydrofuran of refractive index $n_D^{20} = 1.5548$ are obtained.

Preparation of the starting compound

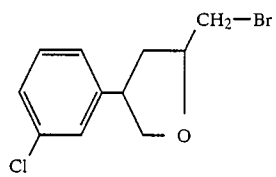

46.3 g (0.26 mol) of N-bromosuccinimide are added in portions with stirring to a solution of 51 g (0.26 mol) of 2-(3-chlorophenyl)-2-allyl-ethanol in 400 ml of absolute chloroform, during which the reaction mixture should warm to 40° C. When the addition is complete, the mixture is stirred for a further 16 hours at room temperature, washed twice with water and dried over sodium sulphate, and the solvent is removed in vacuo.

47 g (66% of theory) of 2-bromomethyl-4-(3-chlorophenyl)-tetrahydrofuran are obtained, and are further reacted directly without purification and isolation.

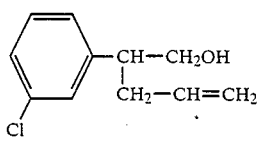

6 g (0.15 mol) of lithium aluminum hydride are added in portions to a solution of 76 g (0.32 mol) of ethyl 2-(3-chlorophenyl)-2-allyl-acetate in 250 ml of absolute ether, the mixture is subsequently stirred at the reflux temperature for 16 hours and then hydrolyzed using concentrated ammonium chloride solution. The organic phase is separated off, dried over sodium sulphate and freed from solvent in vacuo.

51 g (81% of theory) of 2-(3-chlorophenyl)-2-allylethanol (IR: 3200–3300) are obtained and are further reacted directly without further purification and isolation.

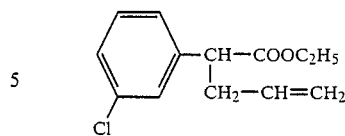

150 g of concentrated sulphuric acid are added dropwise to a solution of 114 g (0.597 mol) of 2-allyl-2-(3-chloro-phenyl)-acetonitrile in 150 ml of ethanol, and the mixture is stirred for 16 hours at a bath temperature of 110° C. after the addition is complete. After cooling, the mixture is poured onto ice and extracted with petroleum ether. The organic phase is washed with sodium hydrogen carbonate solution until neutral, dried over sodium sulphate and freed from solvent in vacuo. The residue is distilled in vacuo.

84 g (59% of theory) of ethyl 2-allyl-2-(3-chlorophenyl)-acetate of boiling point 120° C./0.1 torr are obtained.

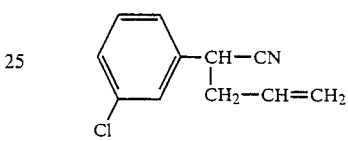

28.7 g (1 mol) of sodium hydride (80%) are added in portions to a solution, cooled to 0° C., of 151 g (1 mol) of 3-chlorobenzyl cyanide in 500 ml of dimethylformamide, during which the temperature is kept between 0° C. and 10° C. by cooling. When the hydrogen evolution is complete, 122 g (1 mol) of allyl bromide are added dropwise at a temperature of 30° C., and the mixture is subsequently stirred for a further 16 hours at 45° C. The reaction mixture is diluted with water and extracted with ether. The organic phase is dried over sodium sulphate and freed from solvent, and the residue is distilled in vacuo.

114 g (60% of theory) of 2-allyl-2-(3-chlorophenyl)acetonitrile of boiling point 91°–95° C./0.1 torr are obtained.

The following 2-aminomethyltetrahydrofurans of the general formula (I) are obtained in a corresponding fashion and according to the general information on the preparation:

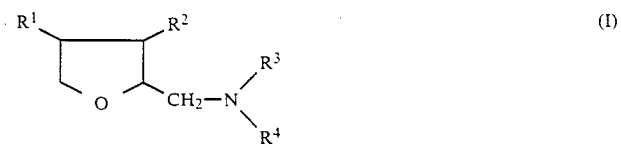

| Example No. | $R^1$ | $R^2$ | $-N\begin{smallmatrix}R^3\\R^4\end{smallmatrix}$ | Physical properties [$n^{20}$ = refractive index or $^1$H NMR] |
|---|---|---|---|---|
| 2 | ![3-CF3-phenyl] | H | -N(morpholino) | 1.5169 |

-continued
$$\begin{array}{c} R^1 \\ \diagdown \\ \end{array} \underset{O}{\overset{R^2}{\diagup}} \text{CH}_2-N\underset{R^4}{\overset{R^3}{\diagdown}} \quad (I)$$
| | R¹ | R² | R³R⁴N- | |
|---|---|---|---|---|
| 3 | 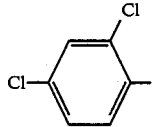 | H | 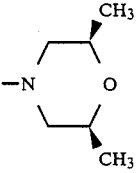 | 1.5430 |
| 4 |  | H | 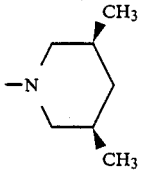 | 1.5456 |
| 5 | 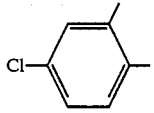 | H | 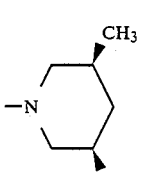 | 4.5–4.8(m)<br>4.1–4.4(m)<br>3.75–3.9(m)<br>3.5–3.7(m) |
| 6 | 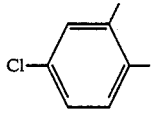 | H | 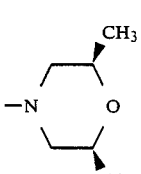<br>× 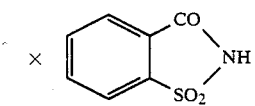 | 4.55–4.8(m)<br>4.1–4.3(m)<br>3.55–4.0(m) |
| 7 | 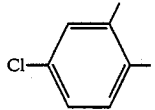 | CH₃ | 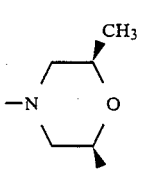 | 1.5503 |
| 8 | 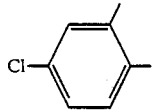 | CH₃ | 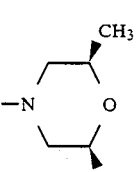<br>× 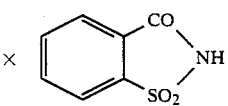 | m.p. 37–42° C. |

-continued

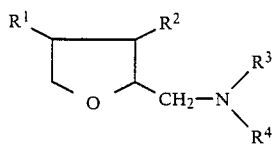
(I)

| Example No. | R¹ | R² | -N(R³)(R⁴) | Physical properties |
|---|---|---|---|---|
| 9 | 2,4-dichlorophenyl | CH₃ | 3,5-dimethylpiperidin-1-yl | 1.5464 |
| 10 | 2,4-dichlorophenyl | CH₃ | 3,5-dimethylpiperidin-1-yl × 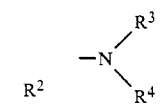 | m.p. 33–37° C. |
| 11 | 2,4-dichlorophenyl | CH₃ | —NH—CH₂—CH(CH₃)₂ | 1.5096 |

| Example No. | R¹ | R² | —N(R³)(R⁴) | Physical properties [$n_D^{20}$ = refractive index or ¹H NMR] |
|---|---|---|---|---|
| 12 | 2,4-dichlorophenyl | CH₃ | morpholin-1-yl | 1.5496 |
| 13 | thien-2-yl | H | 3,5-dimethylpiperidin-1-yl | 1.574 |
| 14 | thien-2-yl | H | 2,6-dimethylmorpholin-1-yl | 1.5259 |
| 15 | 2-fluorophenyl | H | —NH—(CH₂)₃—O—(CH₂)₃—CH₃ | 1.4989 |

-continued
$$\text{(I)}$$
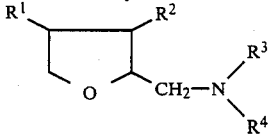
| | R¹ | R² | R³ R⁴ (—N<) | n_D |
|---|---|---|---|---|
| 16 | 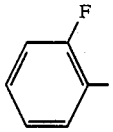 | H | 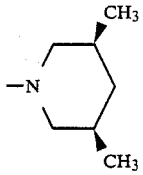 | 1.5151 |
| 17 | 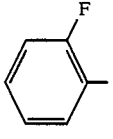 | H | 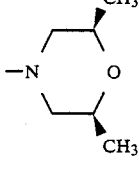 | 1.5130 |
| 18 | 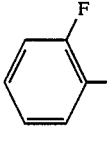 | CH₃ | —NH—(CH₂)₃—O—(CH₂)₃—CH₃ | 1.4961 |
| 19 | 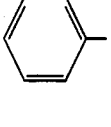 | CH₃ | 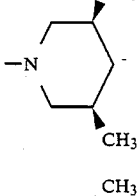 | 1.5120 |
| 20 | 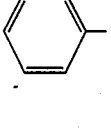 | CH₃ | 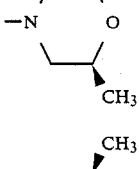 | 1.5089 |
| 21 | 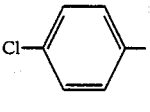 | CH₃ | 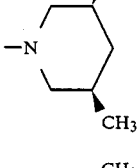 | 1.5261 |
| 22 | 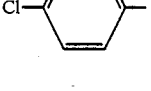 | CH₃ | 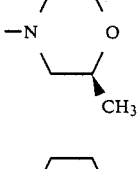 | 1.5275 |
| 23 | 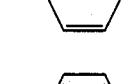 | CH₃ | 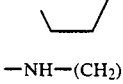 | 1.5348 |
| 24 | 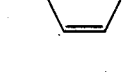 | CH₃ | —NH—(CH₂)₃—C₂H₅ | 1.5993 |

-continued $$\begin{array}{c} R^1 \quad R^2 \\ \diagup \diagdown \\ | \quad | \\ \diagdown O \diagup \\ CH_2-N{\overset{R^3}{\underset{R^4}{}}} \end{array} \quad (I)$$

| | R¹ | R² | NR³R⁴ | |
|---|---|---|---|---|
| 25 | 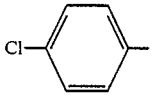 4-Cl-C₆H₄ | CH₃ | —NH—CH₂—CH(CH₃)₂ | 1.5168 |
| 26 | 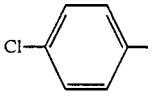 4-Cl-C₆H₄ | CH₃ | —NH—(CH₂)₅—CH₃ | 1.5179 |
| 27 | 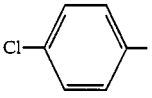 4-Cl-C₆H₄ | CH₃ | 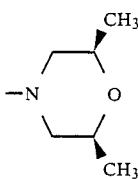 (2,6-dimethylmorpholino) | × 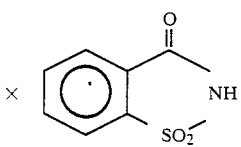 (saccharin) m.p. 32° C. |
| 28 | 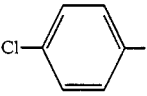 4-Cl-C₆H₄ | CH₃ | 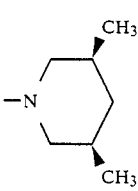 (3,5-dimethylpiperidino) | × 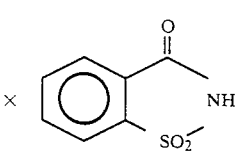 (saccharin) m.p. 35° C. |
| 29 | 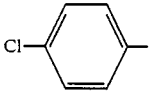 4-Cl-C₆H₄ | CH₃ | 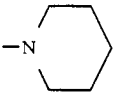 (piperidino) | × 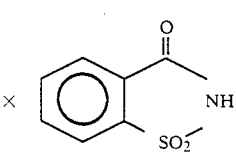 (saccharin) m.p. 33–35° C. |
| 30 | 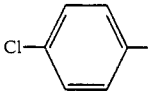 4-Cl-C₆H₄ | CH₃ | —NH—(CH₂)₅—CH₃ | × 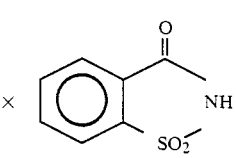 (saccharin) 1.5369 |

-continued
$$\text{(I)}$$
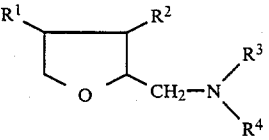
| | R¹ | R² | R³, R⁴ (−NR³R⁴) | |
|---|---|---|---|---|
| 31 | 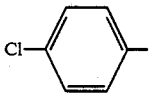 (4-Cl-C₆H₄) | CH₃ | −NH−(CH₂)₃−OC₂H₅ | |
| | | | × 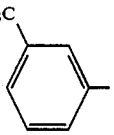 | 1.5348 |
| 32 | 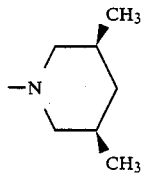 (3-F₃C-C₆H₄) | H | 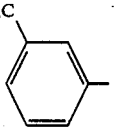 | 1.4826 |
| 33 | 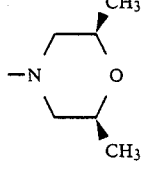 (3-F₃C-C₆H₄) | H | 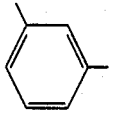 | 1.4869 |
| 34 | 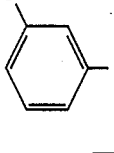 (3-F₃C-C₆H₄) | H | −NH−CH₂−CH(CH₃)₂ | 1.4731 |
| 35 | 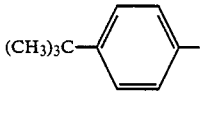 (3-F₃C-C₆H₄) | H | −NH−(CH₂)₃−OC₂H₅ | 1.4769 |
| 36 | 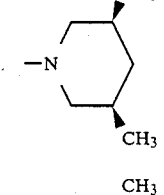 (4-(CH₃)₃C-C₆H₄) | H | 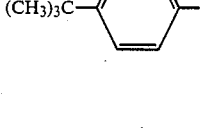 | 1.5104 |
| 37 | 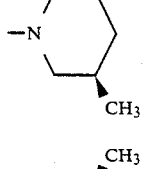 (4-(CH₃)₃C-C₆H₄) | H | 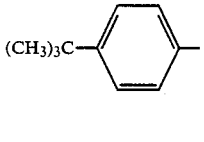 | 1.5099 |
| 38 | 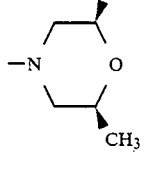 (4-(CH₃)₃C-C₆H₄) | H | (morpholine with 2,6-dimethyl) | |

-continued
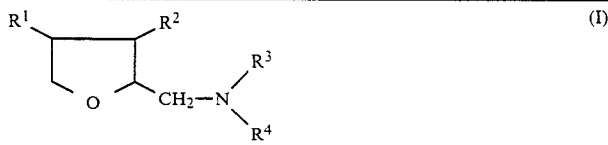 (I)
| | | | | |
|---|---|---|---|---|
| 39 | 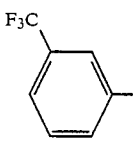 F₃C | H | 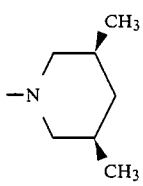 CH₃ ... CH₃ | 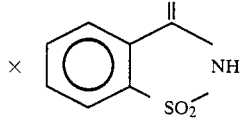 m.p. 41–43° C. |
| 40 | 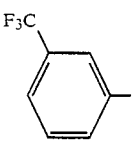 F₃C | H | 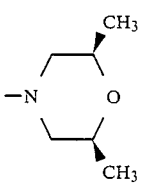 CH₃ ... CH₃ | 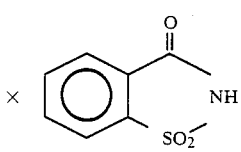 1.5302 |
| 41 | 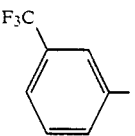 F₃C | CH₃ | 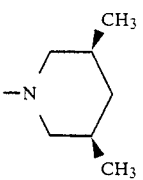 CH₃ ... CH₃ | 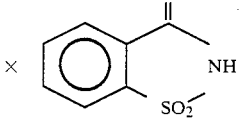 m.p. 31–34° C. 1.4794 |
| 42 | 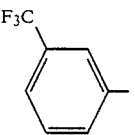 F₃C | H | —NH(CH₂)₃—OC₂H₅ | |
| 43 | 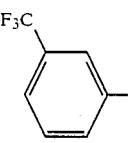 F₃C | CH₃ | 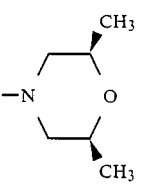 CH₃ ... CH₃ | 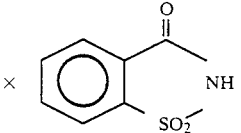 m.p. 30° C. 1.4861 |

-continued $$\underset{\text{(I)}}{\overset{R^1 \quad R^2}{\underset{O}{\bigcirc}}\text{CH}_2-N\overset{R^3}{\underset{R^4}{\diagdown}}}$$

| No. | R¹ | R² | -NR³R⁴ | $n_D$ |
|---|---|---|---|---|
| 44 | 3-(F₃C)-C₆H₄- | CH₃ | —NH—(CH₂)₃—OC₂H₅ | 1.4779 |
| 45 | 4-((CH₃)₃C)-C₆H₄- | CH₃ | 2,6-dimethylmorpholino | 1.5140 |
| 46 | 4-((CH₃)₃C)-C₆H₄- | CH₃ | 3,5-dimethylpiperidino | 1.5155 |
| 47 | 4-((CH₃)₃C)-C₆H₄- | CH₃ | —NH—(CH₂)₃—OC₂H₅ | 1.5050 |
| 48 | 3-(F₃C)-C₆H₄- | CH₃ | —NH—(CH₂)₃—OC₂H₅ | |
| | | | 2-acetyl-benzenesulfonamido (×) | 1.5299 |
| 49 | 4-((CH₃)₃C)-C₆H₄- | CH₃ | cis-2,6-dimethylmorpholino | |
| | | | 2-acetyl-benzenesulfonamido (×) | 1.5340 |
| 50 | 4-((CH₃)₃C)-C₆H₄- | CH₃ | cis-3,5-dimethylpiperidino | |

-continued
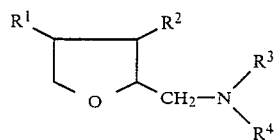
| | R¹ | R² | -NR³R⁴ | |
|---|---|---|---|---|
| | | | ×  benzene with C(=O)-NH and SO₂ (saccharin-like) | 1.5480 |
| 51 | 4-(CH₃)₃C-C₆H₄- | H | 3-methylpiperidin-1-yl | 1.5176 |
| 52 | 3-F₃C-C₆H₄- | CH₃ | 3-methylpiperidin-1-yl | 1.4889 |
| 53 | 3-F₃C-C₆H₄- | CH₃ | 3-methylpiperidin-1-yl  × saccharin | m.p. 36° C. |
| 54 | 4-(CH₃)₃C-C₆H₄- | H | 3-methylpiperidin-1-yl  × saccharin | m.p. 34° C. |
| 55 | 2,4-Cl₂-C₆H₃- | H | -NH-(3-methylcyclohexyl) | 1.5381 |
| 56 | 2,4-Cl₂-C₆H₃- | H | -N(CH₂CH₂OH)₂ | 1.5574 |

-continued $$\begin{array}{c} R^1 \phantom{xxx} R^2 \\ \diagup\!\!\diagdown \\ O \phantom{xx} CH_2-N{\diagup R^3 \atop \diagdown R^4} \end{array} \quad (I)$$

| No. | R¹ | R² | NR³R⁴ | nD |
|---|---|---|---|---|
| 57 | 2,4-dichlorophenyl | H | N(CH₂-C≡CH)(3-methylcyclohexyl) | 1.5474 |
| 58 | 4-tert-butylphenyl | H | 3-methylpiperidin-1-yl × CH₃—(CH₂)₁₁—C₆H₄—SO₃H | |
| 59 | 3-(trifluoromethyl)phenyl | CH₃ | 3-methylpiperidin-1-yl × CH₃—(CH₂)₁₁—C₆H₄—SO₃H | |
| 60 | 4-tert-butylphenyl | H | 3,5-dimethylpiperidin-1-yl × CH₃—(CH₂)₁₁—C₆H₄—SO₃H | |
| 61 | 3-(trifluoromethyl)phenyl | H | N((CH₂)₂—CH₃)(CH₂-tetrahydrofuran-2-yl) | 1.4815 |
| 62 | 4-tert-butylphenyl | H | N((CH₂)₂—CH₃)(CH₂-tetrahydrofuran-2-yl) | 1.5106 |
| 63 | 4-tert-butylphenyl | H | N((CH₂)₂—CH₃)(CH₂-tetrahydrofuran-2-yl) | |

-continued
$$\text{(I)}$$
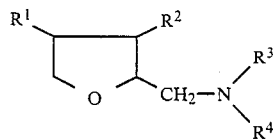
| | $R^1$ | $R^2$ | $\begin{matrix}R^3\\-N\\R^4\end{matrix}$ | |
|---|---|---|---|---|
| | | | 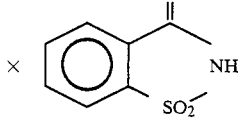 | m.p. 36° C. |
| 64 | 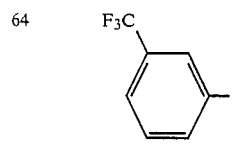 | CH₃ | 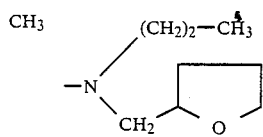 | 1.4822 |
| 65 | 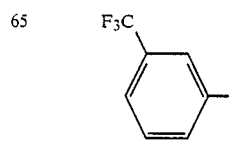 | H | 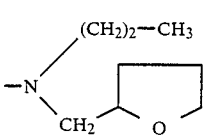 | |
| | | | 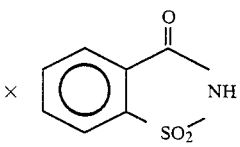 | m.p. 33–36° C. |
| 66 | 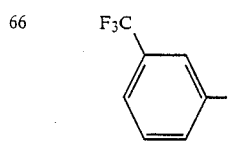 | CH₃ | 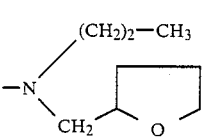 | |
| | | | 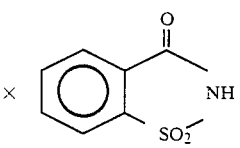 | m.p. 34° C. |
| 67 | 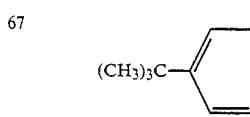 | CH₃ | 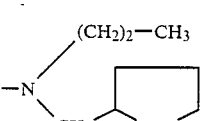 | 1.5121 |
| 68 | 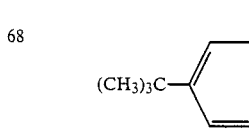 | CH₃ | 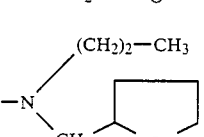 | |
| | | | 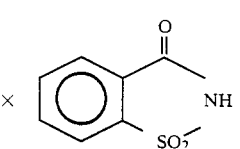 | 1.5415 |
| 69 | 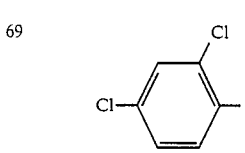 | H | 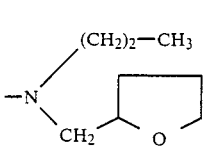 | 1.5405 |

USE EXAMPLES

In the following use examples, the compound shown below is used as comparison substance:

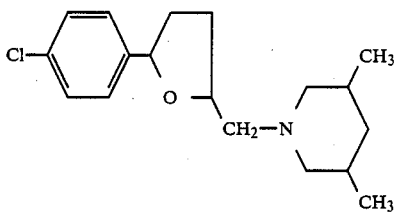
(A)

2-(4-Chlorophenyl)-5-(3,5-dimethylpiperidin-1-ylmethyl)-tetrahydrofuran (cf. U.S. Pat. No. 4,615,725, supra).

EXAMPLE A

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew postules.

Evaluation is carried out 7 days after the inoculation.

In this test, a clearly superior activity compared with the prior art is shown, for example, by the compounds according to preparation Examples 3, 4, 9 and 10.

EXAMPLE B

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to preparation Examples 5, 6 and 8.

EXAMPLE C

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to preparation Examples 5, 6 and 8.

It will be appreciated that the instant specification and examples are set forth by way of illustration and not limitation, and that various modifications and changes may be made without departing from the spirit and scope of the present invention.

What is claimed is:

1. A 2-aminomethyltetrahydrofuran of the formula

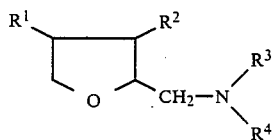

in which
R$^1$ is phenyl substituted by F, mono- and di-Cl, t-butyl or CF$_3$,
R$^2$ is hydrogen or methyl, and
R$^3$ and R$^4$ together with the nitrogen atom to which they are bonded form a dialkyl substituted piperidine or morpholine ring, or
R$^3$ is lower alkyl and R$^4$ is furylmethyl,
or an acid addition salt thereof.

2. A compound according to claim 1, wherein such compound is 2-(2,6-dimethyl-morpholin-4-yl-methyl)-4-(2,4-dichlorophenyl)-tetrahydrofuran of the formula

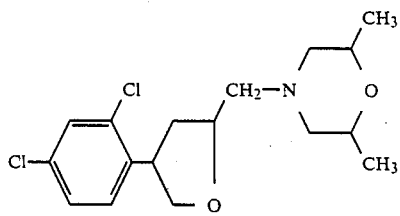

or an acid-addition salt thereof.

3. A compound according to claim 1, wherein such compound is 2-(2,6-dimethyl-morpholin-4-yl-methyl)-3-methyl-4-(3-chlorophenyl)-tetrahydrofuran of the formula

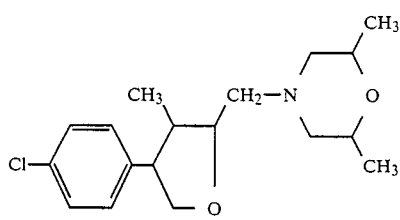

or an acid-addition salt thereof.

4. A compound according to claim 1, wherein such compound is 2-(3,5-dimethyl-piperidin-1-yl-methyl)-3-methyl-4-(4-chlorophenyl)-tetrahydrofuran of the formula

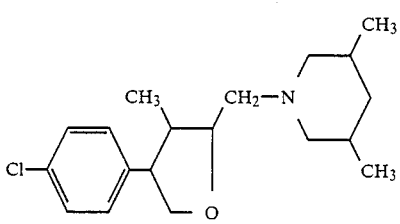

or an acid-addition salt thereof.

5. A compound according to claim 1, wherein such compound is 2-(2,6-dimethyl-morpholin-4-yl-methyl)-4-(3-trifluoromethylphenyl)-tetrahydrofuran of the formula

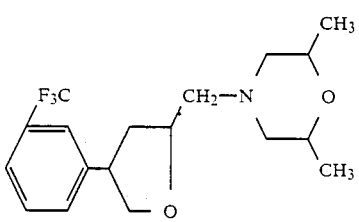

or an acid-addition salt thereof.

6. A compound according to claim 1, wherein such compound is 2-(3,5-dimethyl-piperidin-1-yl-methyl)-4-(4-t-butylphenyl)-tetrahydrofuran of the formula

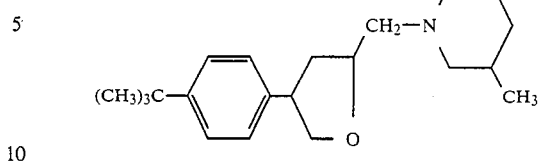

or an acid addition salt thereof.

7. A compound according to claim 1, wherein such compound is 2-[(N-propyl-N-furfuryl)-aminomethyl]-4-(t-butylphenyl)-tetrahydrofuran of the formula

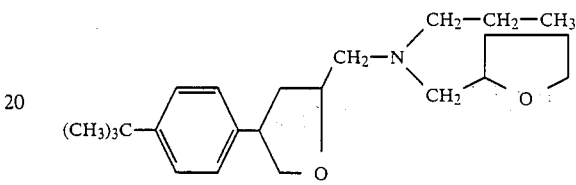

or an acid-addition salt thereof.

8. A fungicidal composition comprising a fungicidally effective amount of a compound or salt according to claim 1 and a diluent.

9. A method of combating fungi which comprises applying to such fungi or to a fungus habitat a fungicidally effective amount of a compound or salt according to claim 1.

10. The method according to claim 9, wherein there is employed 2-(2,6-dimethyl-morpholin-4-yl-methyl)-4-(2,4-dichlorophenyl)-tetrahydrofuran,
2-(2,6-dimethyl-morpholin-4-yl-methyl)-3-methyl-4-(3-chlorophenyl)-tetrahydrofuran,
2-(3,5-dimethyl-piperidin-1-yl-methyl)-3-methyl-4-(4-chloro-phenyl)-tetrahydrofuran,
2-(2,6-dimethyl-morpholin-4-yl-methyl)-4-(3-trifluoromethylphenyl)-tetrahydrofuran,
2-(3,5-dimethyl-piperidin-1-yl-methyl)-4-(4-t-butylphenyl)-tetrahydrofuran, or
2-(ethyoxypropylaminomethyl)-4-(3-trifluoromethylphenyl)-tetrahydrofuran, or
2-[(N-propyl-N-furfuryl)-aminomethyl]-4-(t-butylphenyl)-tetrahydrofuran or an acid-addition salt thereof.

* * * * *